United States Patent [19]

Naumann et al.

[11] 4,256,907
[45] Mar. 17, 1981

[54] PREPARATION OF SUBSTITUTED VINYLCYCLOPROPANE-CARBOXYLIC ACID ESTERS

[75] Inventors: Klaus Naumann, Cologne; Rüdiger Schubart, Berg.-Gladbach; Thomas Schmidt, Wuppertal, all of Fed. Rep. of Germany

[73] Assignee: Bayer Aktiengesellschaft, Leverkusen, Fed. Rep. of Germany

[21] Appl. No.: 899,664

[22] Filed: Apr. 24, 1978

[30] Foreign Application Priority Data

May 11, 1977 [DE] Fed. Rep. of Germany ....... 2721185

[51] Int. Cl.³ .............................................. C07C 67/10
[52] U.S. Cl. ........................... 560/124; 204/158 HA; 568/639; 570/127; 570/182; 570/196
[58] Field of Search ........................................ 560/124

[56] References Cited

U.S. PATENT DOCUMENTS

| | | | |
|---|---|---|---|
| 3,414,607 | 12/1968 | Fajimoto | 560/124 |
| 3,663,591 | 5/1972 | Osbond | 560/124 |
| 3,666,789 | 5/1972 | Itaya | 560/124 |
| 3,758,504 | 9/1973 | Matsui | 560/124 |
| 3,850,977 | 11/1974 | Itaya | 560/124 |
| 4,024,163 | 5/1977 | Elliott | 560/124 |
| 4,061,664 | 12/1977 | Wood | 560/124 |

FOREIGN PATENT DOCUMENTS

| | | | |
|---|---|---|---|
| 768383 | 11/1971 | Belgium | 560/124 |
| 29963 | of 1914 | United Kingdom | 560/236 |
| 633435 | 12/1949 | United Kingdom | 560/236 |
| 1438129 | 6/1976 | United Kingdom | 560/124 |

OTHER PUBLICATIONS

Morrison, "Organic Chemistry," 2nd Ed., pp. 675–678 (1966).
Groggins, "Unit Processes in Organic Synthesis," 4th Ed. pp. 206–207 (1952).
Mazzocchi, J. Am. Chem. Soc., 92, pp. 7220–7221 (1975).
Normant, Synthesis, pp. 805–807 (1975).

*Primary Examiner*—Natalie Trousof
*Assistant Examiner*—Michael Shippen
*Attorney, Agent, or Firm*—Sprung, Felfe, Horn, Lynch & Kramer

[57] ABSTRACT

A process for the preparation of a substituted vinylcyclopropanecarboxylic acid ester of the formula

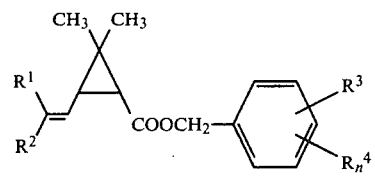

in which
$R^1$ and $R^2$ each independently is alkyl with 1–4 carbon atoms or halogen,
$R^3$ is halogen, phenoxy or phenoxy substituted by alkyl with 1–4 carbon atoms or by halogen,
$R^4$ is halogen or methyl, and
n is 0, 1, 2, 3 or 4, comprising saponifying with alkali an ester of the formula

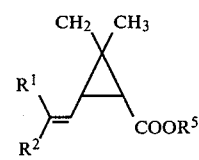

in which
$R^5$ is alkyl with 1–4 carbon atoms, thereby to replace $R^5$ by an alkaline salt group, and directly reacting such salt without intermediate purification with a benzyl chloride of the formula

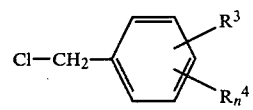

Advantageously the benzyl chloride is obtained by the gas-phase photochlorination of a compound of the formula

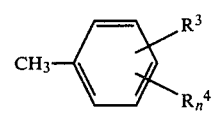

(IV), the chlorination proceeding to about 25 to 75%, and the chlorination mass being employed directly without isolation.

18 Claims, No Drawings

PREPARATION OF SUBSTITUTED VINYLCYCLOPROPANE-CARBOXYLIC ACID ESTERS

The present invention relates to an unobvious process for the preparation of certain insecticidal, substituted vinylcyclopropanoic acid benzyl esters.

It has already been disclosed that substituted vinylcyclopropanecarboxylic acid benzyl esters, in particular 2-(2,2-dichlorovinyl)-3,3-dimethylcyclopropanecarboxylic acid 3-phenoxybenzyl ester, are obtained when the alkali metal salts or tertiary ammonium salts of the corresponding acids are reacted with 3-pheonxybenzyl-triethylammonium bromide (Belgian Patent Specification No. 818,498).

The 3-phenoxybenzyl bromide required as a starting compound for the quaternary salt is available by the process described in DOS (German Published Specification) No. 2,612,115. However, the use of bromine is undesirable for economic and industrial reasons.

Cyclopropanecarboxylic acid benzyl esters can also be prepared from the acid chlorides of these acids and 3-phenoxybenzyl alcohol. However, this alcohol is only available by an involved route, whether by oxidation of 3-phenoxytoluene to give 3-phenoxybenzoic acid and subsequent reduction of the ethyl ester (DOS (German Published Specification) No. 2,604,474) or via a prior side-chain chlorination of 3-phenoxytoluene, which gives a product mixture (DOS (German Published Specification) No. 2,402,457).

The preparation of the acid chlorides thus requires the preparation of the free acids, which are formed by direct acid saponification of the alkyl esters (Coll. Czeck. Chem. Commun. 24, 2230 (1959)), or by alkaline saponification in lower alcohols, after acidifying the salts (DOS (German Published Specification) No. 2,505,398 and DOS (German Published Specification) No. 2,621,830).

Substituted vinylcyclopropanecarboxylic acid esters can be purified by chromatography in a manner which is not very suitable economically (British Patent Specification No. 1,413,491).

It has already been disclosed in Liebigs Annalen der Chemie 688, 28 (1965) and J. Amer. Chem. Soc. 92, 7220 (1970) that above 200° C. vinylcyclopropane derivatives rearrange or undergo a 1,5 hydrogen shift, with extension or opening of the ring.

It was not possible hitherto to prepare substituted vinylcyclopropanecarboxylic acid esters by simple chemical processes, for example by reacting the alkali metal salts of vinylcyclopropanecarboxylic acids with the corresponding benzyl chlorides, since it was not possible to purify the end products economically. It was therefore necessary, in each case, to use starting materials which were as pure as possible, by which corresponding losses in yield already occurred during the preparation of the starting materials. It was also necessary to use starting materials which could be easily purified.

The present invention now provides a process for the preparation of a substituted vinylcyclopropanecarboxylic acid ester of the general formula

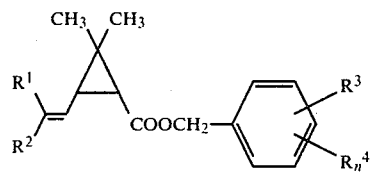

in which $R^1$ and $R^2$, which may be identical or different, each represent alkyl with 1-4 carbon atoms or halogen, $R^3$ represents halogen or phenoxy which is optionally substituted by alkyl with 1-4 carbon atoms or by halogen, $R^4$ represents halogen or methyl and n denotes 0, 1, 2, 3 or 4, in which an ester of the general formula

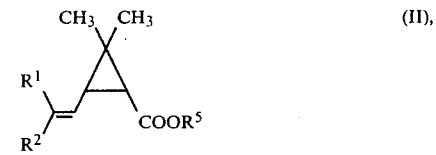

in which $R^1$ and $R^2$ have the meanings stated above and $R^5$ represents alkyl with 1-4 carbon atoms, is subjected to alkaline saponification, and the salt thereby obtained is reacted, without intermediate purification, with a benzyl chloride of the general formula

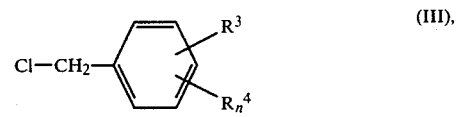

in which $R^3$, $R^4$ and n have the meanings stated above, which is contained in the reaction solution of the gasphase photochlorination of a compound of the general formula

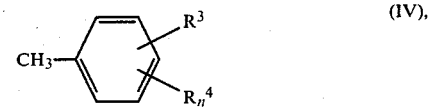

in which $R^3$, $R^4$ and n have the meanings stated above, and the impure substituted vinylcyclopropanecarboxylic acid ester of the general formula (I) thus obtained is distilled between 100° C. and 300° C. under a pressure between $10^{-3}$ mm Hg and normal pressure (760 mm Hg).

By means of this invention, the compounds can be obtained in a pure form by an inexpensive process.

Preferably, $R^1$ and $R^2$, which may be identical or different, each represent methyl, Cl or Br, $R^3$ represents phenoxy which is optionally substituted by F, $R^4$ represents F and n represents 0 or 1.

It has been found that benzyl chlorides of the general formula (III) are obtained by a particularly favorable process in which compounds of the general formula (IV) are subjected to gas phase photochlorination at temperatures between about 200° C. and 300° C.

Furthermore, it has been found that substituted vinylcyclopropanecarboxylic acid esters of the general formula (I) can be obtained in the pure form by distilling them at temperatures between 100° C. and 300° C. under pressures between $10^{-3}$ mm Hg and normal pressure.

It is surprising that the esters of the formula (I) can be distilled without being changed, since from the state of the art it had to be expected that rearrangement would occur.

It is also surprising that the gas-phase chlorination proceeds exclusively in the side chain at a high temperature, since corresponding reactions in the liquid phase at temperatures above about 200° C. under free radical conditions (DOS German Published Specification) No. 2,402,457) lead to a mixture of various products, which also contains 3-phenoxybenzyl chloride.

Furthermore, it is surprising that the reaction of the alkali metal salts with the non-polar reaction solution which is obtained from the gas-phase chlorination proceeds smoothly, without further dilution with a polar solvent, to give the products of the formula (I), since reactions of this type have hitherto been carried out in a polar medium (Synthesis 1975, 805).

The process according to the invention has a number of advantages. The salts first obtained in the alkaline saponification of substituted vinylcyclopropanecarboxylic acid alkyl esters, in general with alkali metal hydroxides in lower alcohols, can be used directly, after removing the solvent, without the corresponding free acids having to be isolated. It is also possible to react the reaction solution formed in the gas-phase photochlorination of compounds of the formula (IV), which contains benzyl chlorides of the formula (III) and unreacted compounds of the formula (IV), without further purification. This means that a pure benzyl chloride of the formula (III) need not be used.

The by-products which may be formed in the course of the reactions and unreacted starting materials can be separated off as a first running or sump product by normal vacuum distillation. The desired esters of the general formula (I) are obtained in the pure form by fractional distillation at temperatures above about 200° C. and pressures of about 0.1 mm Hg.

The preparation of pure 2-(2,2-dichlorovinyl-3,3-dimethylcyclopropanecarboxylic acid 3-phenoxybenzyl ester from 2-(2,2-dichlorovinyl)-3,3-dimethylcyclopropanecarboxylic acid ethyl ester and 3-phenoxytoluene can be represented by the following equation:

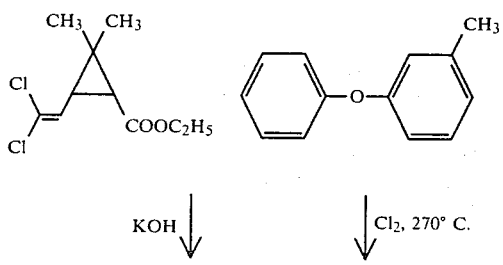

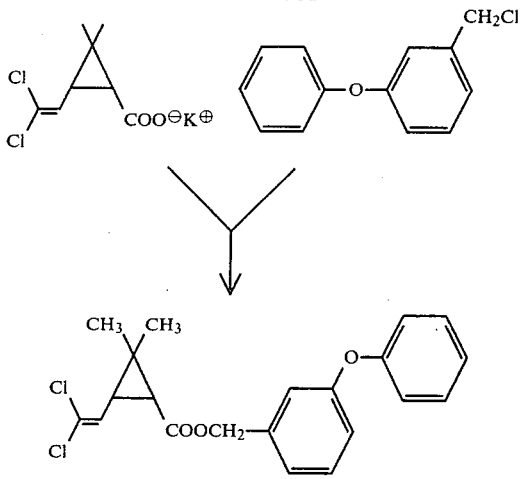

The process according to the invention is particularly suitable for preparing the following compounds in a pure form: 2-(2,2-dichlorovinyl)-3,3-dimethylcyclopropanecarboxylic acid 3-phenoxybenzyl ester, 2-(2,2-dichlorovinyl)-3,3-dimethylcyclopropanecarboxylic acid 3-phenoxy-4-fluoro-benzyl ester, 2-(2,2-dichlorovinyl)-3,3-dimethylcyclopropanecarboxylic acid 3-(4'-fluoro-phenoxy)-benzyl ester, 2-(2,2-dichlorovinyl)-3,3-dimethylcyclopropanecarboxylic acid 3-phenoxy-5-fluoro-benzyl ester, 2-(2,2-dichlorovinyl)-3,3-dimethylcyclopropanecarboxylic acid 3-phenoxy-6-fluoro-benzyl ester, 2-(2,2-dichlorovinyl)-3,3-dimethylcyclopropanecarboxylic acid 3-(3'-fluoro-phenoxy)benzyl ester and 2-(2,2-dichlorovinyl)-3,3-dimethylcyclopropanecarboxylic acid 3-(2'-fluoro-phenoxy)-benzyl ester, and the corresponding esters with 2-(2,2-dibromovinyl)-3,3-dimethyl-cyclopropanecarboxylic acid and with 2-(2-methyl-prop-1-enyl)-3,3-dimethyl-cyclopropanecarboxylic acid.

The starting materials required for the reaction, that is to say the substituted vinylcyclopropanecarboxylic acid alkyl esters or their alkali metal salts and the optionally substituted toluenes or benzyl chlorides, are known and can be prepared analogously to known processes. (See DOS (German Published Specification) No. 2,539,895, DAS (German Published Specification) No. 2,436,178, DOS (German Published Specification) No. 2,604,474 and DOS (German Published Specification) No. 2,402,457).

The process, which is also according to the invention, of the gas phase photochlorination of the compounds of the general formula (IV) is carried out without using a diluent or other auxiliaries in a manner such that the dry compounds of the formula (IV) are boiled, and dry chlorine gas, diluted with inert gas, such as nitrogen or argon, is passed in in the vapor phase, optionally in the presence of UV rays. The reaction temperature for the gas phase reaction is between about 200° C. and 400° C.; the boiling point of the appropriate compounds of the formula (IV) is the preferred reaction temperature, e.g. about 270° C. The reaction can also be carried out under a slight vacuum, as well as under slightly elevated pressure. 0.1 to 1 mol of chlorine is generally employed per mol of compound of the formula (IV). However, the reaction is preferably carried out only up to a degree of chlorination of about 25% to 75%. The benzyl chlorides of the formula (III) can be obtained in the pure form by fractionating the reaction solution. However, the reaction solution directly obtained is suitable for further use in the process according to the invention.

Examples of benzyl chlorides which can be prepared by the gas phase chlorination according to the invention are: 3-phenoxybenzyl chloride, 3-phenoxy-4-fluoro-benzyl chloride, 3-phenoxy-5-fluoro-benzyl chloride, 3-phenoxy-6-fluoro-benzyl chloride, 3-phenoxy-6-chloro-benzyl chloride, 3-phenoxy-6-bromo-benzyl chloride, 3-phenoxy-5-methyl-benzyl chloride, 3-(4'-fluoro-phenoxy)-benzyl chloride, 3-(3'-fluoro-phenoxy)-benzyl chloride, 3-(2'-fluoro-phenoxy) benzyl chloride, 3-(4'-chloro-phenoxy) benzyl chloride, 3-(3'-chloro-phenoxy)-benzyl chloride, 3-(2'-chloro-phenoxy)-benzyl chloride, 3-(2'bromo-phenoxy)-benzyl chloride, 3-(3'-bromo-phenoxy)-benzyl chloride and 3-(4'-bromo-phenoxy)-benzyl chloride.

In order to prepare salts of substituted 2-vinyl-3,3-dimethylcyclopropanecarboxylic acids, the corresponding methyl or ethyl esters can be completely saponified by boiling for several hours with equivalent amounts of NaOH or KOH in methanol, optionally in the presence of a few equivalents of water. This procedure can be accelerated by applying pressure at elevated temperatures.

Preferably, however, a compound of the formula (IV), for example 3-phenoxytoluene, can be employed as the reaction medium for the saponification, using NaOH powder or KOH powder and carrying out the reaction at temperatures between about 50° and 180° C., preferably about 80° to 150° C. The course of the saponification can then be followed by means of the methanol or ethanol which distils over. The short reaction times (about 30 minutes) are advantageous for this saponification variant. The reaction mixture thus obtained contains the alkali metal salts of the corresponding carboxylic acids in the form of a suspension and can be reacted directly with the reaction solution of the abovementioned gas phase chlorination, just as the residue from the concentrated reaction solution of the alcoholic saponification can. The stoichiometric ratio of alkali metal salt to chloromethyl compound is at least 1:1. Pentamethyldiethylenetriamine or tetramethylethylenediamine, for example, can optionally be added as a catalyst, as is described in Synthesis 1975, page 805.

For the complete formation of the substituted vinylcyclopropane carboxylic acid esters of the formula (I), the mixture is heated at from about 20° C. to 150° C., preferably about 60° C. to 120° C., usually for about 3 to 5 hours. After separating off the inorganic by-products by filtration or extraction by shaking with water, the reaction mixture is distilled in vacuo as described above, in order to obtain the pure products of the formula (I).

The reactions described can also be carried out by adding the appropriate amounts of the carboxylic acid ethyl ester or methyl ester and NaOH or KOH powder as well as the catalyst to the reaction solution of the chlorination, heating the mixture and then isolating the product as indicated above.

Unreacted compounds of the formula (III), which in some cases have been used as the reaction medium and in certain circumstances contain small proportions of, inter alia, nuclear-chlorinated products, can be recycled to the chlorination or saponification, if appropriate after intermediate purification, a continuous reaction procedure being achieved.

The resulting pure compounds (I) are very active insecticides (Nature 246, 5429 (1973), Agr. Biol. Chem. 37, 2681 (1973), DOS (German Published Specification) 2,547,534 and Agr. Biol. Chem. 40, 247 (1976).

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages or development. The above-mentioned pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., Bucculatrix thurberiella, Phyllocnistis citrella, Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimi-*

*lis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., Monomorium pharaonis and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* and from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize corn and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The process of the present invention is illustrated by the following preparative examples:

EXAMPLE 1

Alkaline saponification of 2-(2,2-dichlorovinyl)-3,3-dimethylcyclopropanecarboxylic acid ethyl ester with methanolic KOH:

1 mol of 2-(2,2-dichlorovinyl)-3,3-dimethylcyclopropanecarboxylic acid ethyl ester was boiled with 1 mol of KOH in 0.5 liter of $CH_3OH$ in the presence of 5 mol of water for 10 hours. The mixture was concentrated in vacuo to give a saponaceous mass consisting of the potassium salts.

EXAMPLE 2

Alkaline saponification of 2-(2,2-dichlorovinyl)-3,3-dimethylcyclopropanecarboxylic acid methyl ester with NaOH in 3-phenoxytoluene:

0.2 mol of 2-(2,2-dichlorovinyl)-3,3-dimethylcyclopropanecarboxylic acid methyl ester was heated to 135° C. in 300 ml of 3-phenoxytoluene together with 0.2 mol of NaOH dust for 30 minutes, methanol being distilled off. The suspension of the sodium salts formed was further used for the reaction described in Example 4.

EXAMPLE 3

Gas phase chlorination of 3-phenoxytoluene:

0.75 mole of dry 3-phenoxytoluene was heated to the boil in a distillation flask with a 30 cm packed column and, set on top of this, a reaction zone with a gas inlet frit, an irradiation region and a condenser. 0.25 mol of dry chlorine gas, diluted with nitrogen in the ratio 1:1, was then passed into the hot vapor above the column, while irradiating with a mercury lamp. According to analysis by gas chromatography, the contents of the reaction flask contained, in addition to 3-phenoxytoluene, 3-phenoxybenzyl chloride in 95% purity. The reaction of the chlorine to give 3-phenoxybenzyl chloride was thus almost quantitative. Distillation in vacuo left no residue.

EXAMPLE 4

Preparation of 2-(2,2-dichlorovinyl)-3,3-dimethylcyclopropanecarboxylic acid 3-phenoxybenzyl ester:

Variant a

The suspension of the sodium salt of 2-(2,2-dichlorovinyl)-3,3-dimethylcyclopropanecarboxylic acid in 3-phenoxytoluene obtained in Example 2 was heated to 100° C. with the reaction solution from Example 3, which contained 3-phenoxybenzyl chloride in 3-phenoxytoluene as the solvent, together with 10 g of pentamethyl-diethylenetriamine for 5 hours. The mixture was filtered, the residue was rinsed with 3-phenoxytoluene and the constituents in the filtrate which boiled up to 150° C. were first separated off in a thinfilm evaporator in vacuo under 0.1 mm Hg. The higher-boiling runnings were then fractionated; boiling point 190°–210° C./0.1 mm Hg.

The spectroscopic data were in agreement with authentic samples (DOS (German Published Specification) No. 2,539,895).

Yield, relative to methyl ester originally employed: 88%.

Variant b

3-Phenoxytoluene was reacted with 0.3 mol of $Cl_2$ according to Example 3 in a manner such that the reaction solution contained 0.28 mol of 3-phenoxybenzyl chloride after the chlorination. 0.28 mol of 2-(2,2-dichlorovinyl)-3,3-dimethylcyclopropanecarboxylic acid ethyl ester and 0.28 mol of NaOH dust as well as 0.01 mol of pentamethyldiethylenetriamine were added to the reaction solution, and the mixture was heated to 130° C. for 5 hours whereupon 0.28 mol of ethanol was initially distilled off. After working up as described above, the desired product was obtained after distillation.

It will be appreciated that the instant specification and examples are set forth by way of illustration and not limitation, and that various modifications and changes may be made without departing from the spirit and scope of the present invention.

What we claim is:

1. A process for the preparation of a substituted vinyl-cyclopropanecarboxylic acid ester of the formula

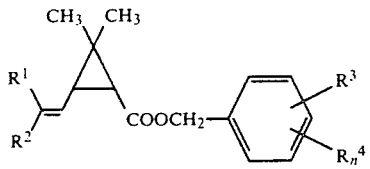

in which
$R^1$ and $R^2$ each independently is alkyl with 1–4 carbon atoms or halogen,
$R^3$ is halogen, phenoxy or phenoxy substituted by alkyl with 1–4 carbon atoms or by halogen,
$R^4$ is halogen or methyl, and
n is 0, 1, 2, 3 or 4,
comprising saponifying with alkali an ester of the formula

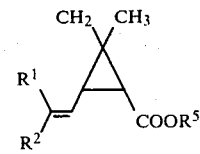

in which
$R^5$ is alkyl with 1–4 carbon atoms,
thereby to replace $R^5$ by an alkaline salt group, photochlorinating a compound of the formula

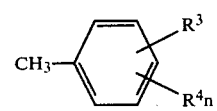

by reacting it directly in the gas phase at a temperature above about 200° C. with chlorine gas diluted with an inert gas to produce a benzyl chloride of the formula

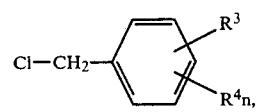

and directly reacting such salt and said benzyl chloride without intermediate purification.

2. A process according to claim 1, in which
$R^1$ and $R^2$ each independently is methyl, Cl or Br,
$R^3$ is phenoxy or fluorophenoxy,
$R^4$ is F, and
n is 0 or 1.

3. A process according to claim 2, in which $R^5$ is methyl or ethyl.

4. A process according to claim 1, in which the saponifying alkali is an alkali metal hydroxide.

5. A process according to claim 1, in which the saponification is effected by boiling the ester with sodium hydroxide or potassium hydroxide in an alcoholic solution.

6. A process according to claim 5, in which the solution is in methanol.

7. A process according to claim 1, in which the saponification is effected using sodium hydroxide powder or potassium hydroxide powder, the reaction medium being a compound of the formula

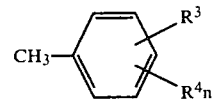

8. A process according to claim 7, in which the saponification is effected at about 50° to 180° C.

9. A process according to claim 8, in which the saponification is effected at about 80° C. to 150° C.

10. A process according to claim 1, in which the ester and alkali are added to the solution of the gas-phase photochlorination and are reacted in situ.

11. A process according claim 1, in which the gas-phase photochlorination is effected by vaporizing the dry compound to be chlorinated and reacting the vapor with the chlorine gas diluted with the inert gas, the reaction zone being irradiated with UV light.

12. A process according to claim 11, in which 0.1 to 1 mol of chlorine is employed per mol of the compound to be chlorinated.

13. A process according to claim 1, in which the degree of chlorination in the gas-phase photochlorination of the compound to be chlorinated is about 25% to 75%.

14. A process according to claim 1, in which the reaction between the salt and the benzyl chloride is effected at about 20° to 150° C.

15. A process according to claim 1, in which the reaction between the salt and the benzyl chloride is effected at about 60° to 120° C.

16. A process according to claim 1 in which the reaction between the salt and the benzyl chloride is catalyzed by pentamethyldiethylenetriamine or tetramethylethylenediamine.

17. A process according to claim 1, including the further step of purifying the impure substituted vinylcyclopropanecarboxylic acid ester by distilling said ester at a temperature between about 100° C. and 300° C. under a pressure between about $10^{-3}$ mm Hg and normal pressure.

18. A process according to claim 3, in which the saponifying alkali is sodium hydroxide or potassium hydroxide, the ester and alkali are added to the solution of the gas-phase photochlorination and are reacted in situ, the gas-phase photochlorination is effected by vaporizing the dry compound to be chlorinated and reacting the vapor at about 200° to 300° C. with sufficient chlorine diluted with the inert gas so as to effect about 25 to 75% chlorination, the reaction zone being irradiated with UV light, the reaction between the salt and the benzyl chloride is effected at about 60° to 120° C. catalyzed by pentamethyldiethylenetriamine or tetramethylethylenediamine, and distillation of the benzyl ester is effected at a temperature between about 100° C. and 300° C. under a pressure between about $10^{-3}$ mm Hg and normal pressure.

* * * * *